(12) United States Patent
Norton

(10) Patent No.: US 6,988,416 B1
(45) Date of Patent: *Jan. 24, 2006

(54) SHOE TESTING APPARATUS AND METHOD OF OPERATION

(76) Inventor: Craig Norton, 6830 Ridgewood Dr., Oakland, CA (US) 94611

(*) Notice: Subject to any disclaimer, the term of this patent is extended or adjusted under 35 U.S.C. 154(b) by 0 days.

This patent is subject to a terminal disclaimer.

(21) Appl. No.: 10/855,781

(22) Filed: May 28, 2004

(51) Int. Cl.
*G01N 3/08* (2006.01)

(52) U.S. Cl. ...................................................... 73/818
(58) Field of Classification Search ................ 73/847, 73/794, 7, 788, 818; 36/29; 12/142 R
See application file for complete search history.

(56) References Cited

U.S. PATENT DOCUMENTS

| | | | |
|---|---|---|---|
| 3,005,218 A * | 10/1961 | Johnston | 12/142 R |
| 6,289,743 B1 | 9/2001 | Norton | |
| 6,739,200 B1 | 5/2004 | Norton | |
| 6,820,353 B2 * | 11/2004 | Oman et al. | 36/29 |

* cited by examiner

Primary Examiner—Max Noori
Assistant Examiner—Octavia Davis
(74) Attorney, Agent, or Firm—Tom Hamill, Jr.

(57) ABSTRACT

A device for testing, measuring and indexing shoes is disclosed. The device measures the capacity for vertical support of the midsole which is located directly under the heel of the foot. A base value is established for a specific brand and model of shoe. This permits the consumer to compare the amount of cushioning and shock absorption during the heel strike phase of running or walking activities of any of a plurality of different brand and models of shoe. Further, one may determine the value of a shoe which has been used to determine whether it should be replaced. The device employs a heel ram which would be inserted into the shoe directly above the midsole where the heel of the foot would reside. The ram is then forced into the midsole material. When a specific amount of pressure is achieved (PSI), a sensor measures the depth of penetration into the material. The less depth that is reached with the predetermined pressure, the more structure there is in the midsole. A greater depth (at the predetermined pressure) on the same brand and model of shoe would indicate that there is less structure (and structural integrity) in the midsole. This would give the consumer an independent assessment of the quality of either a used shoe or a new shoe with respect to other shoes in the same class. The device may also measure the decrease in vertical support of the midsole due to increased temperature and compression forces. This device may be employed singly or in combination with a torsional shoe testing device.

9 Claims, 7 Drawing Sheets

SHOE TESTING APPARATUS AND METHOD OF OPERATION

BACKGROUND OF THE INVENTION

1. Field of the Invention

The present invention relates to testing devices which measure the material properties of footwear. More specifically, the testing device measures the capacity for vertical support of the midsole of the shoe. Although the testing device may be employed with any footwear, it may find its greatest use in measuring and categorizing the data from sports or athletic footwear. It is also contemplated that the measuring device will measure the deterioration of vertical support of the midsole with the increase of temperature, the age of shoe itself, as well as the stresses that the shoe has been put through. These measurements will permit the consumer to find a shoe (or athletic footwear) that demonstrates the best value by comparison of the test results. This testing device may be employed with the torsional testing device of U.S. Pat. No. 6,289,743 and U.S. Pat. No. 6,739,200 which are incorporated by reference. Both these aforementioned patents have the same inventor.

2. Description of the Prior Art

A variety of shoe testing devices are known in the art. These have been discussed in U.S. Pat. No. 6,289,743 which has been incorporated by reference. None of the devices known employ a mechanism to measure the capacity for vertical support of an athletic shoe at the midsole. Nor do any of the known devices measure the capacity for vertical support with temperature variation. U.S. Pat. No. 6,289,743 measures the torsional stresses and the resistance to axial twisting motion in the shoe. A second patent by the same inventive entity measures the torsional stresses with increased temperature (U.S. Pat. No. 6,739,200). These two patents measure completely different shoe properties and it is intended to employ one testing machine to test all of these properties and perhaps others not yet discussed.

Athletic shoes, in the last thirty years or so, have progressed from the canvas "high-top chucks" to today's computer designed athletic footwear often costing over $100.00 USD, at the time of this application for patent. Other than the price itself, it is difficult to categorize such footwear. Materials used to manufacture the footwear, the method of manufacture thereof and the intended use of the footwear are several of the parameters which can be categorized, indexed and classified by the instant invention. It has become known that the capacity for vertical support at the midsole is an important measurement in such athletic footwear. When new, the amount of support at the midsole is at its maximum. The material(s) that the midsole is comprised of and the amount of such material is often one of the main factors in determining its longevity, resistance to heat, moisture and other stressors. By using the instant invention, one may make a comparison chart of new athletic shoes as well as test used athletic shoes to see if they are still within a certain parameter which would maintain performance and minimize injury.

SUMMARY OF THE INVENTION

A device for testing, measuring material properties and indexing and displaying how the shoes measure up with respect to each other is disclosed. Generally, midsoles are made out of various densities of EVA, polyurethane and other materials. These materials vary from one manufacturer to another. The shoe measuring device ascertains the capacity for vertical support of the midsole material which is located directly under where the heel of the foot would reside. By using the shoe testing apparatus one may easily determine a base value for a specific brand and model of shoe. This base value permits the consumer to compare the amount of cushioning and shock absorption during the heel strike phase of running or walking activities of any of a plurality of different brand and models of shoe. Further, one may determine the value of a shoe which has been used to determine whether it should be replaced. The device employs a heel ram which would be inserted into the shoe directly above the midsole where the heel of the foot would reside. The ram is then forced into the midsole material. When a specific amount of pressure is achieved (PSI), a sensor measures the depth of penetration into the material. The less depth that is reached with the predetermined pressure, the more structure there is in the midsole. A greater depth (at the predetermined pressure) on the same brand and model of shoe would indicate that there is less structure (and structural integrity) in the midsole. This would give the consumer an independent assessment of the quality of either a used shoe or a new shoe with respect to other shoes in the same class. The invention will also be used to measure the decrease in vertical support of the midsole due to increased temperature. This device may be employed singly or in combination with a torsional shoe testing device. The measured variables may be charted for shoes in specific price ranges, shoes for specific sports, i.e. running shoes, cross-training shoes, cycling shoes, general walking shoes etcetera. This will permit the consumer to choose the best shoe for the desired sport.

Although it would be easy to compare brand name shoes in their new state to determine the better grades versus the poorer ones, the instant device can also determine if a current worn show is still up to proper specifications. One could employ a chart which shows the properties of shoe A when it is in brand new condition. Then it could be compared to a second shoe A which has been used for example for jogging for 6 months. For example if 70 or 80 percent of the original structure of the midsole is remaining, the shoes may not necessarily need to be replaced. Alternatively, if there is only 50 percent of the original structure, the shoe is no longer functioning as designed. Recall that the measurement being taken in this step is the distance a ram will travel into the material at a certain pressure (PSI). The material may have worn or broken down due to temperature extremes, moisture, or sweat. Other environmental stressors on the shoe would include water that has been run through by the user. Of these factors, and others, it appears as if temperature is one which deteriorates the structure of the midsole, or at least the ability of the midsole to support pressure.

In order to use the instant apparatus to quantify and measure the decrease in vertical support in the midsole of a shoe due to increased temperatures, two methods have been developed. The first method is controlled environment testing or CET. In this method, the first temperature of the athletic shoe is ascertained. The vertical structure of the midsole is tested and recorded at the first temperature. Then the temperature of the environment is raised at a predetermined rate to a second temperature. When the shoe's temperature is equal to that of the new environmental temperature, the vertical structure of the midsole is tested and the results recorded at the higher temperature. The percentage difference between the absolute value of measurement taken at the first temperature and the measurement taken at the second higher temperature is called the percent of shoe breakdown, or fatigue factor.

A second version of the test is called kinetic temperature testing (KTT). Again, an initial temperature is recorded and the vertical structure of the midsole is tested and is recorded at that first temperature. Then, the athletic shoe would go through a predetermined time period of vigorous activity (running, jumping, hiking and the like). Then a second temperature is recorded and a second test of the vertical structure of the midsole is made. The difference between the measured vertical structure in the midsole at both temperatures is considered the breakdown of the shoe. This can be defined as a percent of breakdown since the original values of the new shoe have already been determined. The KTT may be considered a more realistic test as the shoes are put through the paces of running, jumping, vertical forces and such, as well as moisture effects, the moisture at least being generated by sweat. Either method would permit one to categorize shoes by any of a variety of factors, including, but not limited to, price, type, size, manufacturer, intended use and the like.

The above brief description sets forth broadly the most important features of the present invention. There are additional features of the invention that will be described herein and which will form the subject matter of the claims of the invention.

In this respect, before explaining the invention in detail, it is to be understood that the invention is capable of other embodiments and of being practiced and carried out in various ways. Additionally, the terminology employed herein is for the purpose of description and should not be considered limiting. As such, those skilled in the art will appreciate that the conception, upon which this disclosure is based, may readily be utilized as a basis for designing other structures, methods, and systems for carrying out the several purposes of the instant invention. It is considered important that the claims be regarded as including equivalent constructions insofar as they do not depart from the spirit and scope of the present invention.

DETAILED DESCRIPTION OF THE INVENTION

With reference now to the drawings, a new and improved shoe testing apparatus and method for use embodying the principles and concepts as well as the preferred embodiment of the invention will be described.

Figure 1:
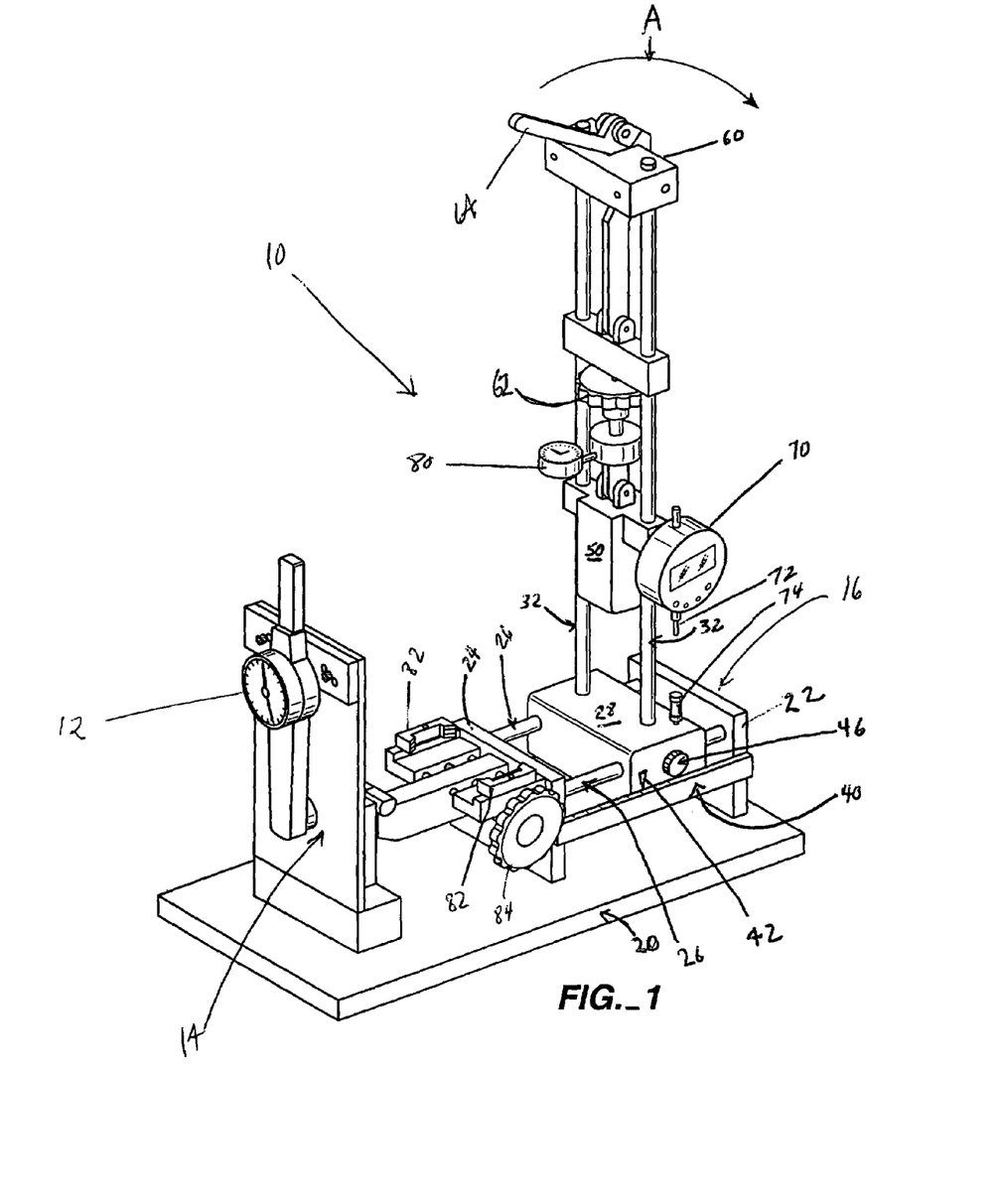
FIG. 1 is a perspective view of the shoe testing apparatus of the invention.
Figure 2:
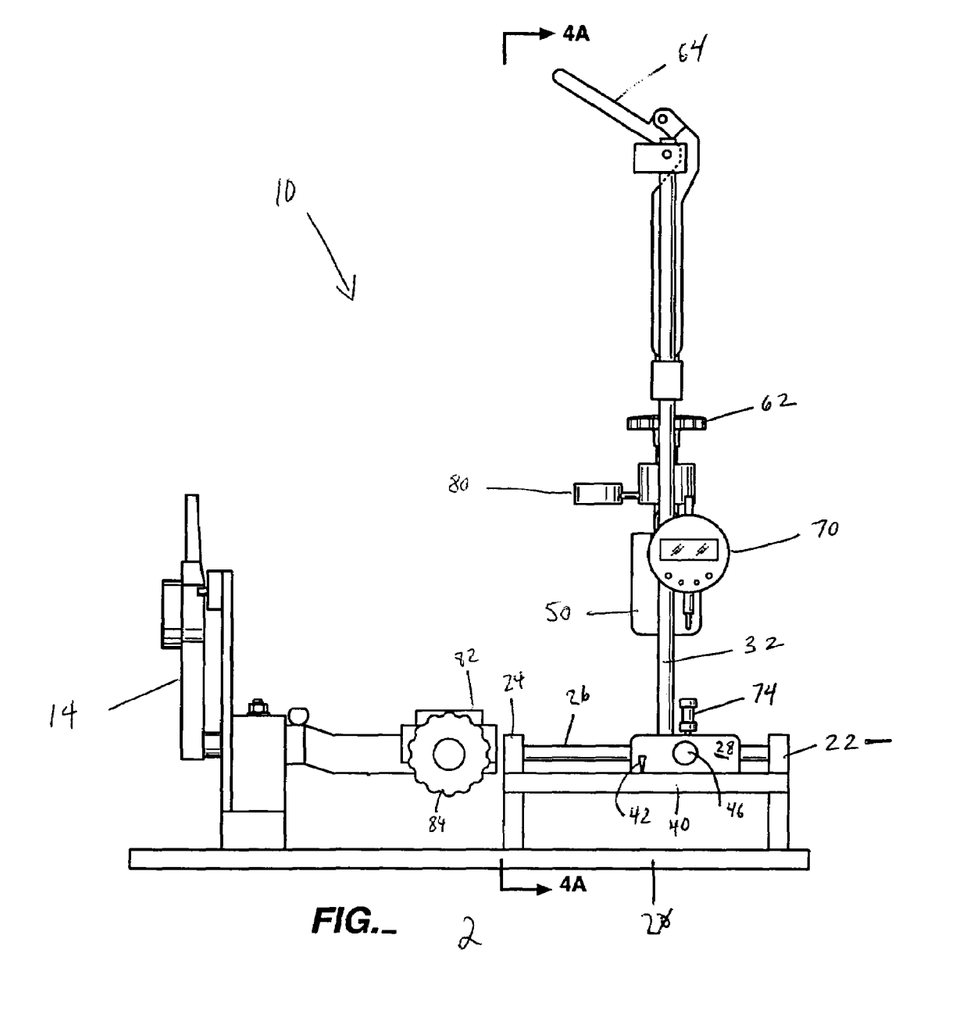
FIG. 2 is a side view of the shoe testing apparatus of the invention.

Referring first to FIGS. 1 & 2, the shoe testing apparatus 10 of the instant invention is shown. The shoe testing apparatus 10 is designed to test the material properties of the material that the midsole is composed of. This can be done when the shoe is in a new condition. This would allow one to compare new shoes with respect to this value. Additionally, one may test new shoes after they have been exposed to a plurality of conditions, such as temperature change, moisture change or other factors. Further, one may test a used shoe to ascertain whether or not the vertical support of the midsole material is within its proper design parameters.

This device includes means to test other properties of the shoe, such as the torque required to axially rotate the front portion of a shoe, as described in U.S. Pat. No. 6,289,743. The torque measuring subsystem 12 is shown as the instant invention will be able to make such measurements. The instant device may or may not have the torsion testing device affixed.

The apparatus 10 sits on a generally rectangular base 20. To simplify matters throughout this discussion, the apparatus 10 will have a front indicated at 14 in the Figures and a rear indicated at 16 in the Figures. A rear heel block support plate 22 and a front heel block support plate 24 are provided. Both plates 22 & 24 are fixed perpendicularly to the base 20. Extending between the rear heel block support plate 22 and the front heel block support plate 24 are a first pair of parallel rails 26. In the embodiment described herein, these parallel rails 26 are cylindrical in shape, but it should be understood that other shapes, for instance rectangular or I beam cross-sections could be employed as well. Riding on these rails is the heel support plate 28. Heel support plate 28 is slidably disposed on the rails 26 and has an action of movement from the rear heel support plate 22 to the front heel support plate 24. By this sliding action, any shoe size may be accommodated in the apparatus 10. Element 40 is attached to both the rear heel support plate 22 and the front heel support plate 24. Element 40 includes a rule which can indicate shoe sizes or any desired length of measure. The heel support plate 28 includes pointer 42. This indicates where the heel support plate 28 is with respect to the front heel support plate 24. This also indicates where the heel support plate 28 is with respect to the rear heel support plate 22. This ruler may be marked in shoe sizes for ease of loading a shoe into the test device. Heel support plate 22 includes securing means 46, which in this embodiment is a manually turned knob. Securing means 46 locks the heel support plate 28 on the first pair of parallel rails 26 in any desired position.

A second pair of parallel rails 32 extend upwardly from the heel support plate 28. Supported on the second pair of rails is the heel ram 50. Affixed atop the heel ram 50 is an over center cam lever carrier mechanism 60. Intermediate the heel ram 50 and the over center cam lever carrier mechanism 60 is a vertical adjustment means 62.

The over center cam lever carrier mechanism 60 supports a lever 64. When lever 64 is actuated by rotation about Arrow A, the over center cam lever carrier mechanism 60 and the heel ram 50, as well as the vertical adjustment means 62 are all moved downward by a predetermined amount.

Located proximal the heel ram 50 is a distance measuring device 70. The distance measuring device 70 measures how far the heel ram 50 would penetrate into the midsole material of the shoe. The distance measuring device includes probe 72 which is adapted to be received in aperture 74. The distance the probe 72 travels in the aperture 74 is directly proportional to the distance traveled by the heel ram 50. The distance measuring device 70 may be any mechanical, electrical, electromechanical linear distance measuring device.

Located proximal to the vertical adjustment means 62 is a pressure measuring device 80. This would measure the pressure applied at a specific distance of penetration into the midsole material of the shoe.

A shoe clamping mechanism 82 is also provided. This structure is described in U.S. Pat. No. 6,289,743 which is incorporated by reference. The shoe clamping mechanism 82 clamps the shoe exteriorly and securely generally about the widest portion of the shoe.

Figure 3A:
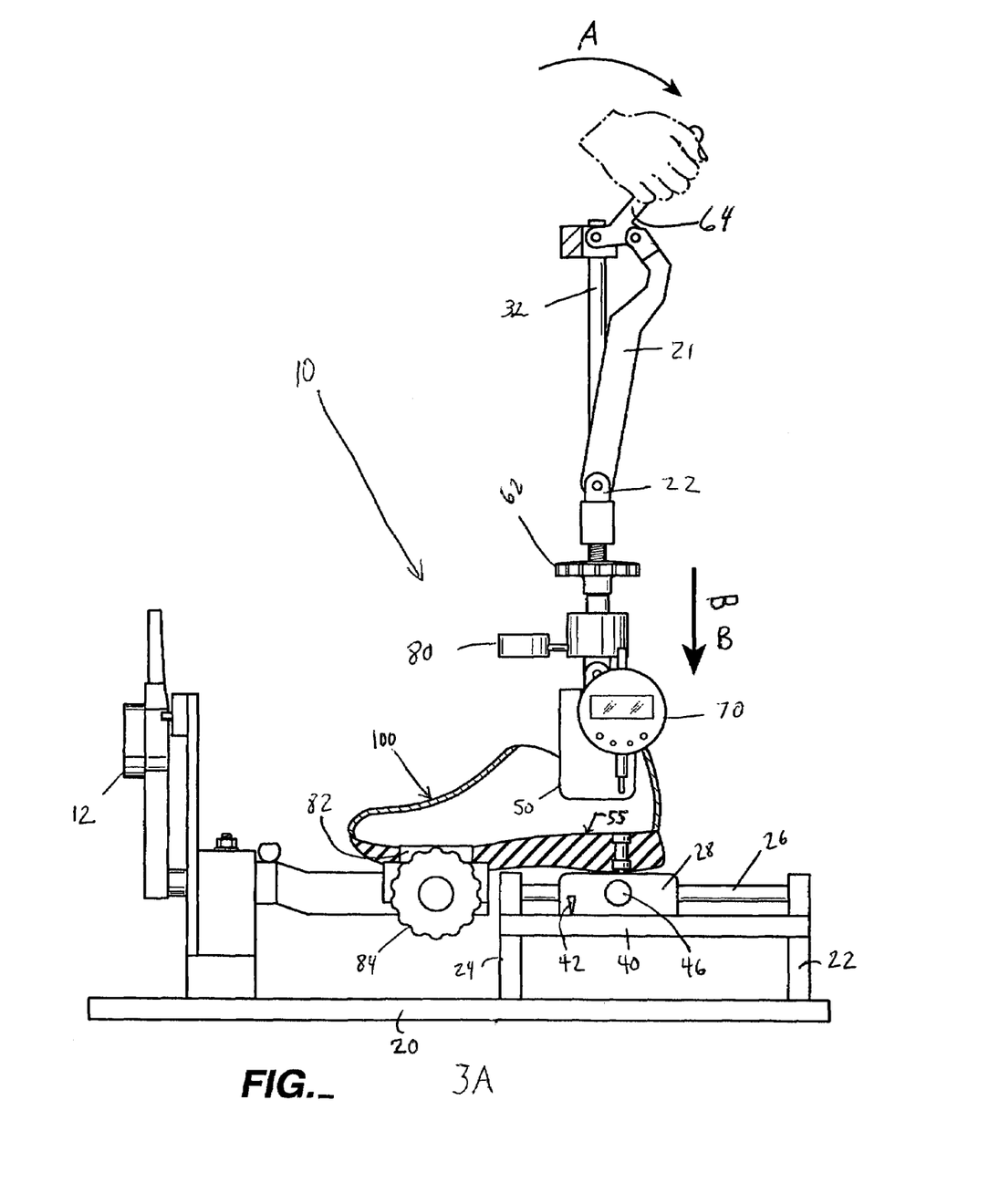
FIG. 3A is a side view of the shoe testing apparatus of the invention, showing a cutaway side view of the shoe loaded in the apparatus at the beginning of a test cycle.

Referring now to FIG. 3A, a substantially side view of the shoe measuring apparatus 10 is shown. Shoe 100 is shown in cross-section. Heel support plate 28 has been positioned to an appropriate location on rails 26 and is secured by tightening securing means 46. The exterior shoe clamping means 82 is also secured. At this point the shoe 100 is secured in the shoe testing device 10. At this point, lever 64 is actuated causing the heel ram 50 to move downward (Note arrow B) and enter into the shoe 100. At this point, the shoe ram 50 is not in contact with the midsole material 55 atop the heel of the shoe. Both the pressure gauge 80 and the depth gauge 70 read zero.

Figure 3B:
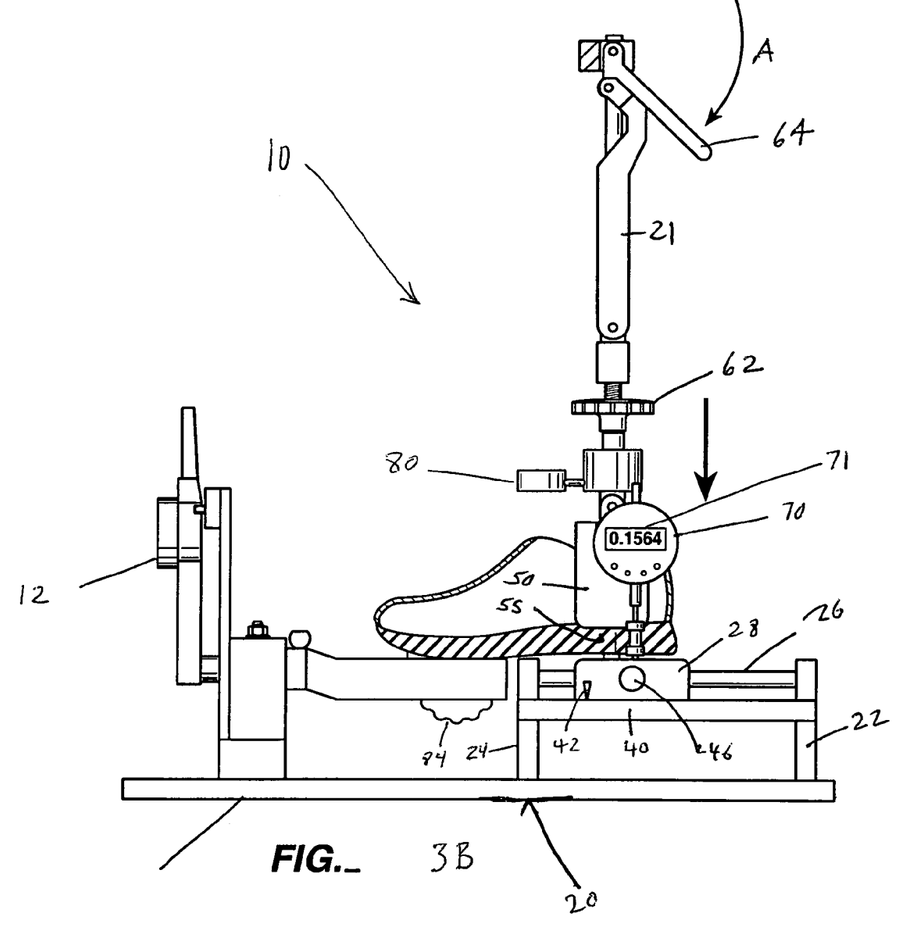
FIG. 3B is a side view of the shoe testing apparatus of the invention, showing a cutaway side view of the shoe during the test cycle, the gauge (caliper) displaying the depth the heel ram penetrates the vertical structure of the midsole.

Referring now to FIG. 3B, lever 64 has been fully actuated. At this point vertical adjustment means 62 further displaced the shoe ram 50 in a downward direction into the midsole material 55 atop the heel of the shoe. The shoe ram 50 is moved until pressure gauge 80 reads a predetermined pressure. At this point, the depth gauge 70 is read. In this Figure, the vertical displacement of the midsole material 55 atop the heel of the shoe is shown to be 0.1564 inches. A ratio of the pressure to the displacement would give a figure that can be compared to other shoes. In this fashion, shoes can be rated, and the information may be used to help a purchaser or even a shoe designer.

Figure 4A:
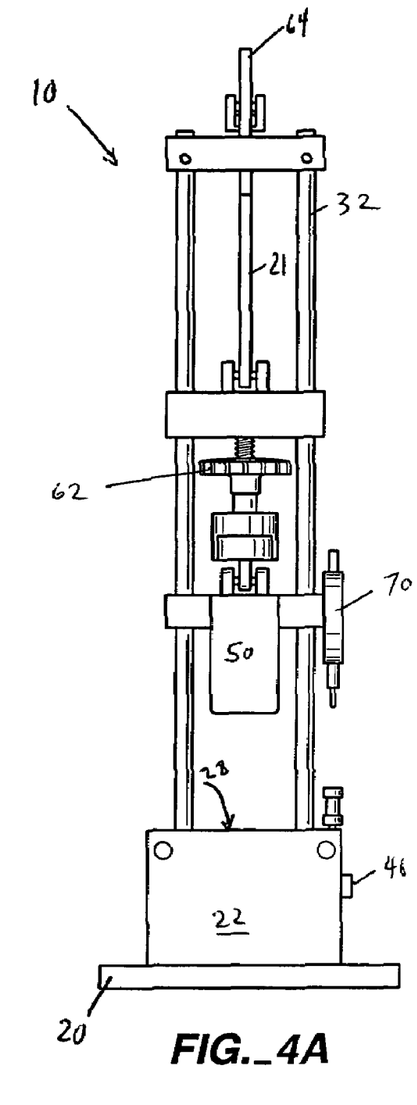
FIG. 4A is a rear view of the shoe testing apparatus showing the apparatus prior to the loading of a shoe to be tested.
Figure 4B:
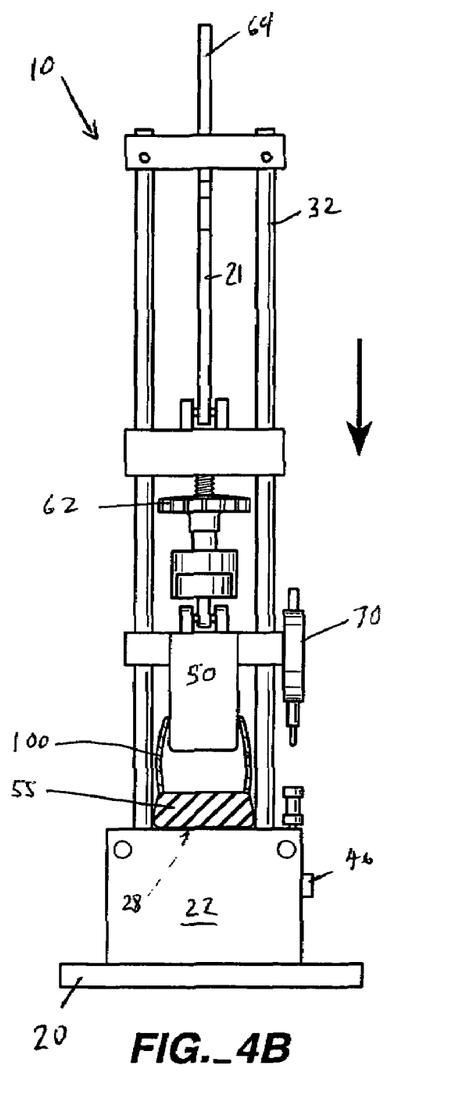
FIG. 4B is a rear view of the shoe testing apparatus showing a cutaway rear view of the shoe loaded into the apparatus at the beginning of the test cycle.
Figure 4C:
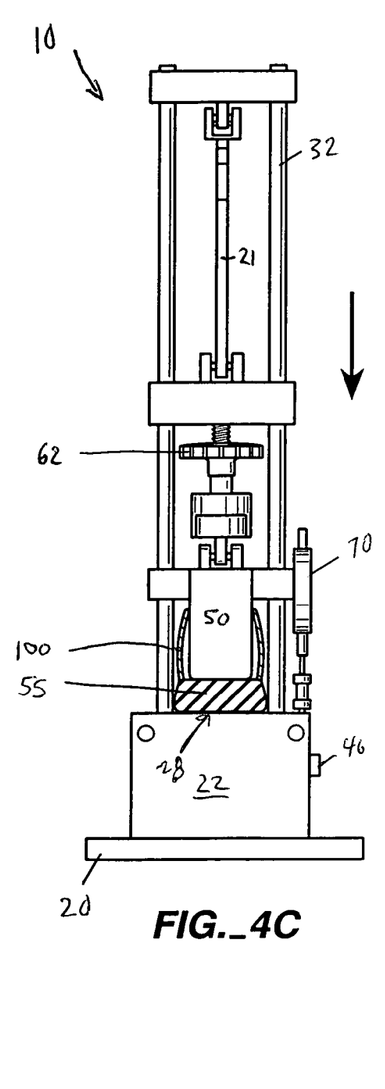
FIG. 4C is a rear view of the shoe testing apparatus showing a cutaway rear view of the shoe, with the heel ram locked down flush against the vertical structure of the midsole.
Figure 4D:
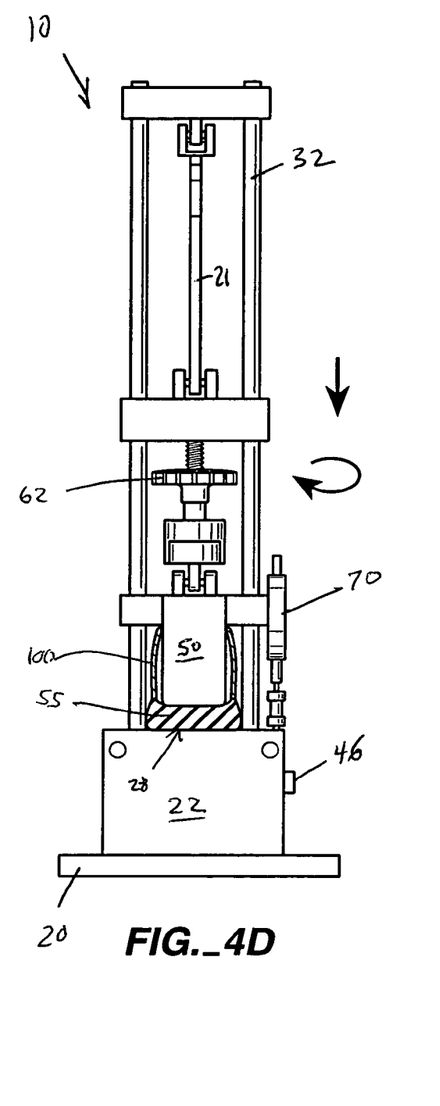
FIG. 4D is a rear view of the shoe testing apparatus, showing a cutaway rear view of the shoe, with the heel ram penetrating the vertical structure of the midsole.

FIGS. 4A–4D show the action of the heel press mechanism through the cycle of the test. The heel press mechanism includes the vertical rails 32, the lever 64, the over center cam mechanism 60, the mechanical linkages (21 & 22), the vertical adjustment means 62, the pressure gauge 80, the depth gauge 70, the shoe ram 50 and the heel support plate 28. FIG. 4A shows the test device 10 unloaded. FIG. 4B shows the shoe 100 resting atop the heel support plate 28, with lever 64 being actuated, which downwardly moved the shoe ram 50 into the shoe. FIG. 4C shows the lever 64 fully deployed and the vertical adjustment means 62 being employed to fine tune the shoe ram 50 so that it lies directly atop the midsole material 55 atop the heel of the shoe. FIG. 4D shows the shoe ram 50 displacing the midsole material 55 atop the heel of the shoe. This is accomplished by rotating the vertical adjustment means 62 to a predetermined pressure. At this point, the vertical distance is read off the depth gauge 70. After this, the vertical adjustment means 62 is counter-rotated, and the lever 64 pulled back, unloading the shoe 100. Measurements may be compared against a base line and the shoe evaluated. It is to be understood that other linkage assemblies, vertical displacement mechanisms, pressure and distance sensors may be employed and are considered to be within the scope of this invention.

Figure 5:
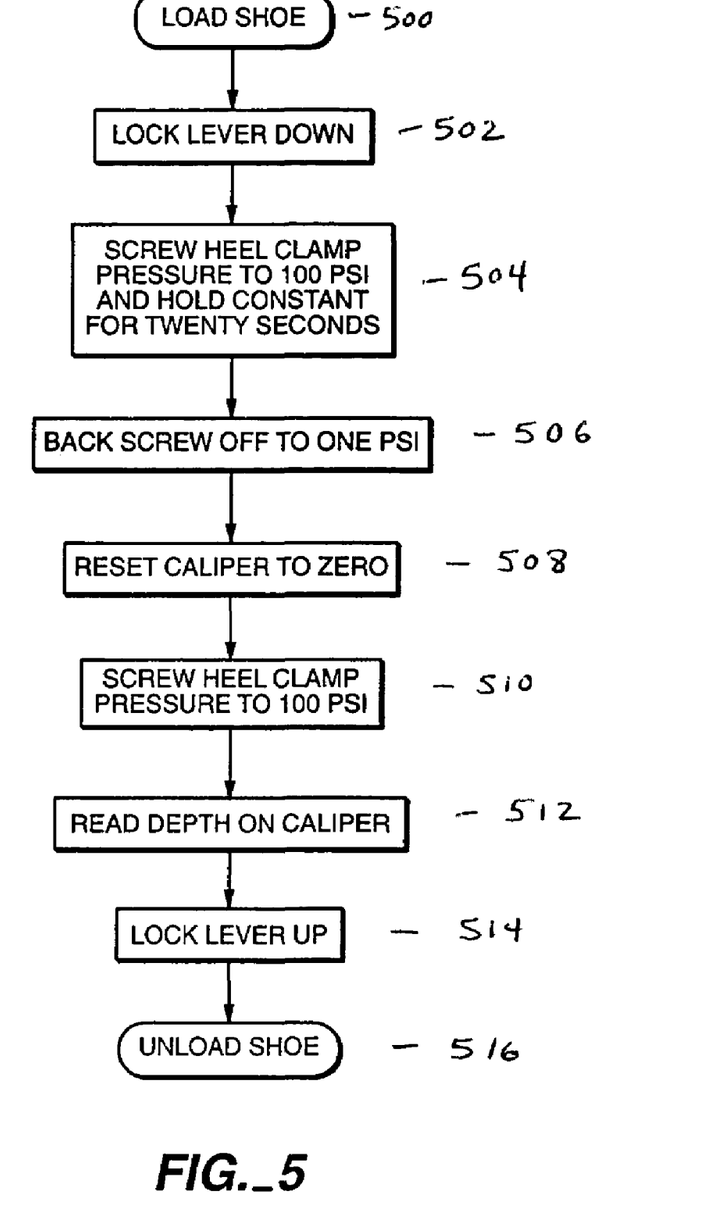
FIG. 5 is a block diagram describing the steps of a shoe testing cycle.

Referring now specifically to FIG. 5, a flowchart showing the steps taken to measure and quantify the vertical support structure of the midsole lying under the heel of the foot is shown. It is to be understood that other test methods may be employed.

First the shoe is loaded 500. This includes aligning the shoe 100 in the horizontal clamps 82, and securing them about the shoe 100 by rotating adjustment knob 84. The heel support plate 28 is placed and secured under the heel of the shoe 100. This causes heel ram 50 to be directly over the midsole material located interior the shoe atop the heel.

Second, the lever is locked down 502, which means that lever 64 is pulled back (as best seen in FIG. 1) and the heel ram 50 is moved down proximal the top layer of the midsole material above the heel. Adjustment of the position of the heel ram 50 is made by rotating the vertical adjustment means 62. The heel ram 50 should be residing on top of the midsole material above the heel, and the pressure (force) measuring device should read zero.

The third step is the first compression step 504. The vertical adjustment means 62 is rotated until the pressure gauge 80 reads 100 psi. This is held for a first time period, for example 20 seconds. This first compression step 504 stresses the midsole material, as well as the surrounding material, stitching, adhesives etcetera. The first time period is designed to force excess air to exit the midsole portion of the shoe.

The fourth step is the back off step 506. After the first compression step 504 is complete, the vertical adjustment means 62 is adjusted until the pressure gauge reads 0 psi.

The fifth step 508 is to reset the caliper 70 to read zero. At this point, there is 0 psi pressure being applied to the midsole material above the heel, and the depth of penetration of the heel ram 50 is determined to be zero.

The sixth step 510 is the second compression step. Here the vertical adjustment means 62 is adjusted again until the pressure gauge reads 100 psi.

The seventh step 512 is the measuring step. The vertical distance the heel ram travels into the midsole material above the heel is displayed on the caliper 70 or other linear distance measuring device. This value is recorded.

The eighth step 514 is to unlock lever 64 and return it to it's original position.

The ninth step 516 is to unload the shoe 100 from the apparatus 10.

At this point, one has a measurement which may be indexed for shoe type. These measurements may be compared for different types of shoes. The midsole under the heel is important in absorbing shock during the heel strike phase of running or walking activities. Thus individuals of heavier stature, those predisposed to heavy exercise regimes, and others benefit from more vertical structure in the midsole to achieve proper cushioning and shock absorption during the heel strike phase. Those of lighter stature benefit from less structured midsoles that more easily compress, giving them more cushion and shock absorption during heel strike. The instant invention gives an independent measure of this important feature and permits a shoe to be literally be prescribed to the user by one who has access to this data.

The above steps may be performed on new or used shoes, at room temperature or at other temperatures, before a variety of kinetic activities are performed thereon or after. Further, other measurements may be taken as described in the patents that are incorporated by reference.

As mentioned previously, this invention can be used to quantify and measure the decrease in vertical support of the midsole of a shoe due to increased temperature. There are two testing methods associated with the increase of temperature in the shoe. The first would be termed controlled environment testing (CET). The temperature of the athletic shoe or the like is ascertained by conventional means. The vertical structure of the midsole above the heel is tested by the above method and the result recorded. The temperature of the shoe is increased gradually to the desired second temperature. The vertical structure of the midsole above the heel is tested at the second temperature and the second result recorded. The percent difference in measurement is called the percent of shoe breakdown.

The second version of the temperature test is called the kinetic temperature test (KTT). Here the temperature of the shoe is also ascertained by conventional means and then the vertical structure of the midsole above the heel is tested by the above method and the result recorded. Then, the shoe undergoes a period or vigorous activity (e.g. running, biking, hiking). The temperature and vertical structure of the midsole above the heel is tested at this second temperature and the second result recorded. Again, the percent difference in measurement is defined as the breakdown of the shoe.

It is to be understood that the steps shown in FIG. 5 are for example only. The testing apparatus may be used in any of a variety of steps, with different time periods, pressures, temperatures, kinetics etc. For instance the shoe may be immersed in water and then tested. As long as the test methodology is standardized, one may compare one shoe to another in an independent fashion.

Further, it is contemplated that the instant invention and the previous test devices described in the patents incorporated by reference may be employed on a single mechanical test apparatus. Additionally, such an apparatus may be automated. The test apparatus may be computer controlled, programmable to perform any test methodology. It could perform the tests sequentially, directing the sensor data to be displayed on a computer in graphical form. This can be accomplished through the use of motors, to rotate the shoe for torsion testing, as well as move the shoe ram up and down according to the instructions of the computer or microprocessors.

With respect to the above description, it should be realized that the optimum dimensional relationships for the parts of the invention, to include variations in size, materials, shape, form, function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiment of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed is:

1. A shoe measuring apparatus to be used with a shoe having a heel, an inner heel surface, a midsole including a cushioning layer, and front side portions comprising,
   a base,
   a shoe heel support portion attached to said base,
   a heel ram, said heel ram provided with means to indicate a pressure and said heel ram further provided with means to indicate the depth of penetration of said heel ram into said cushioning layer of the midsole above the heel, whereby when said heel ram is actuated a measurement of the vertical support of said midsole atop the heel can be determined.

2. The shoe measuring apparatus according to claim 1 wherein said shoe heel support portion further includes a slidable heel support portion, said slidable heel support portion being mounted on rails over said base, said rails extending between a heel block rear plate and a heel block front plate, and said heel block front plate and said heel block rear plate are attached to said base, and where said slidable heel support portion is slidable between said heel block rear plate and said heel block front plate, and further where said slidable heel support portion includes a top surface for engaging the heel of the shoe.

3. The shoe measuring apparatus according to claim 2 wherein said slidable heel support portion includes a pair of vertical rails extending upwardly from said top surface of said slidable heel support portion, said vertical rails engaging said heel ram, said heel ram slidable on said vertical rails, said heel ram adapted to fit inside the shoe and said heel ram further adapted to be adjusted to reside on top of said cushioning layer of the midsole above the heel in the shoe.

4. The shoe measuring apparatus according to claim 3, further including an overeater cam lever attached to said heel ram, where activating the said overeater cam lever presses said heel ram into the opening above the heel of the shoe.

5. The shoe measuring apparatus according to claim 4, further including a heel ram adjustment means which causes said heel ram to compress said cushioning layer of the midsole above the heel in the shoe.

6. The shoe measuring apparatus according to claim 5 wherein a shoe front clamping portion is attached to said base, said shoe front clamping portion fixedly engages the front side portions of the shoe.

7. A shoe measuring apparatus to be used with a shoe having a heel and a midsole comprising;
   a base,
   a shoe heel support portion attached to said base,
   said shoe heel support portion including means for fixedly engage a shoe heel,
   said shoe heel support portion further including a slidable heel block support portion,
   said slidable heel block support portion being mounted on rails over said base,
   said rails extending between a heel block rear plate and a heel block front plate where said heel block rear plate and said heel block front plate are attached to said base,
   and where said slidable heel block support portion is slidable between said heel block rear plate and said heel block front plate,
   and further where said slidable heel block support portion includes an upper surface for engaging the heel of the shoe,
   and further where said shoe heel support portion includes a pair of vertical rails extending upwardly from said upper surface,
   said vertical rails engaging a heel press mechanism slidable on said vertical rails,
   said heel press mechanism further including a heel ram adapted to fit inside the shoe,
   said heel press mechanism further including an overeater cam lever attached to said heel ram, where activating said overeater cam lever displaces said heel ram into said shoe, said heel press mechanism further including a depth adjustment device, permitting said heel ram to move vertically and compress the midsole of the shoe above the heel of the shoe, said heel press mechanism including a pressure sensor and a depth sensor, wherein a pressure measurement and a depth measurement can be obtained when said heel ram displaces the midsole material of the shoe above the heel of the shoe.

8. A method for measuring the vertical support capacity of the midsole material located atop the heel of an athletic shoe comprising the steps of:

providing a planar platform;

securing the shoe atop said planar platform;

providing a ram means to engage said midsole material located atop the heel;

compressing said midsole material located atop the heel by vertically displacing said ram means;

providing a means for measuring pressure and a means for measuring vertical linear displacement during the compressing step;

observing said means for measuring pressure and said means for measuring vertical linear displacement.

9. The method of claim 8, further comprising the step of:

providing a visual pressure readout means on said means for measuring pressure and a visual vertical linear distance readout means on said means to measure said vertical linear displacement.

* * * * *